US008432540B2

(12) United States Patent
Kuo et al.

(10) Patent No.: US 8,432,540 B2
(45) Date of Patent: Apr. 30, 2013

(54) SUPPORT MECHANISM FOR INSPECTION SYSTEMS

(75) Inventors: Cooper S. K. Kuo, Taipei (CN); Ron Tsai, Taipei (CN); Steven Lee, Taipei (CN)

(73) Assignee: Cooper S.K. Kuo, Taipei (TW)

( * ) Notice: Subject to any disclaimer, the term of this patent is extended or adjusted under 35 U.S.C. 154(b) by 308 days.

(21) Appl. No.: 12/751,605

(22) Filed: Mar. 31, 2010

(65) Prior Publication Data

US 2011/0240579 A1     Oct. 6, 2011

(51) Int. Cl.
*G01N 21/00* (2006.01)
(52) U.S. Cl.
USPC .............. 356/237.1; 356/239.1; 356/431; 382/141
(58) Field of Classification Search .......... 248/127; 211/169, 96; 382/141, 112; 358/474; 356/237.1, 356/421, 239.1; 324/750.19, 760.01
See application file for complete search history.

(56) References Cited

U.S. PATENT DOCUMENTS

| | | | | |
|---|---|---|---|---|
| 2,916,151 | A * | 12/1959 | Roush | 211/40 |
| 3,351,211 | A * | 11/1967 | Best | 211/169 |
| 3,420,381 | A * | 1/1969 | Bradfield | 211/26 |
| 3,754,146 | A * | 8/1973 | Chow | 250/559.48 |
| 4,891,530 | A * | 1/1990 | Hatji | 250/559.4 |
| 4,989,981 | A * | 2/1991 | Kawamura et al. | 356/394 |
| 5,691,764 | A * | 11/1997 | Takekoshi et al. | 348/86 |
| 6,320,654 | B1 * | 11/2001 | Alders et al. | 356/237.2 |
| 6,340,092 | B1 * | 1/2002 | McGrath, Jr. | 211/169 |
| 6,362,884 | B1 * | 3/2002 | Okahira et al. | 356/399 |

(Continued)

FOREIGN PATENT DOCUMENTS

| | | |
|---|---|---|
| JP | 2000-342957 A | 12/2000 |
| JP | 2001-255232 A | 9/2001 |

(Continued)

OTHER PUBLICATIONS

European Search Report from European Application No. 10 16 3863, dated Apr. 19, 2012.

(Continued)

*Primary Examiner* — Terrell McKinnon
*Assistant Examiner* — Daniel J Breslin
(74) *Attorney, Agent, or Firm* — Alston & Bird LLP (57) ABSTRACT

A support mechanism includes a first work frame to provide a first scanning area for a first scanner, a first frame to support a first panel, the first frame pivotably coupled to a first end of the first work frame so that the first frame is rotatable about the first end of the first work frame between a folded position that the first frame is folded toward the first scanning area and an unfolded position that the first frame is away from the first scanning area, and a second frame to support a second panel, the second frame pivotably coupled to a second end of the first work frame so that the second frame is rotatable about the second end of the first work frame between a folded position that the second frame is folded toward the first scanning area and an unfolded position that the second frame is away from the first scanning area, wherein the first scanning area allows the first scanner to scan across one of the first and second frames when the one of the first and second frames is at the folded position while the other one of the first and second frames is at the unfolded position.

7 Claims, 7 Drawing Sheets

U.S. PATENT DOCUMENTS

| | | | | |
|---|---|---|---|---|
| 6,671,041 B2* | 12/2003 | Okahira et al. | | 356/237.1 |
| 6,707,546 B2* | 3/2004 | Okahira et al. | | 356/239.1 |
| 6,879,180 B2* | 4/2005 | Iwata et al. | | 324/750.22 |
| 7,110,104 B2* | 9/2006 | Choi et al. | | 356/237.1 |
| 7,675,625 B2* | 3/2010 | Yoon | | 356/445 |
| 8,049,879 B2* | 11/2011 | Shetterly et al. | | 356/239.2 |
| 8,289,389 B2* | 10/2012 | Yoon et al. | | 348/131 |
| 2001/0002862 A1* | 6/2001 | Okahira et al. | | 356/237.1 |
| 2005/0018897 A1* | 1/2005 | Choi et al. | | 382/141 |
| 2006/0175275 A1* | 8/2006 | Israel et al. | | 211/169 |
| 2006/0220670 A1* | 10/2006 | Huang et al. | | 324/770 |
| 2007/0152701 A1* | 7/2007 | Yoon | | 324/770 |
| 2007/0159160 A1* | 7/2007 | Yoon et al. | | 324/158.1 |
| 2009/0282871 A1* | 11/2009 | Shetterly et al. | | 65/29.12 |
| 2011/0235868 A1* | 9/2011 | Kuo et al. | | 382/112 |
| 2011/0240579 A1* | 10/2011 | Kuo et al. | | 211/169 |

FOREIGN PATENT DOCUMENTS

| | | |
|---|---|---|
| JP | 2004-340666 A | 12/2004 |
| JP | 2005-017179 A | 1/2005 |
| JP | 2006-300913 A | 2/2006 |
| JP | 2006-184019 A | 7/2006 |

OTHER PUBLICATIONS

Japan Application No. 2010-169805, First Office Action dated Feb. 28, 2012.

* cited by examiner

SUPPORT MECHANISM FOR INSPECTION SYSTEMS

BACKGROUND OF THE INVENTION

The invention generally relates to optical inspection and, more particularly, to a support mechanism for use in an optical inspection system.

Display devices such as liquid crystal display (LCD) devices are used for electronically displaying information including text, images and moving pictures. An LCD may include a number of layers such as polarized filter, glass substrate, color filter, liquid crystal and reflective surface, which may determine the quality of the LCD. To examine whether an LCD is a qualified one, human eye inspection may sometimes be employed. However, eye inspection may mean time-consuming, laborious and imprecise in the mass-production of LCDs. Moreover, with the advance in semiconductor manufacturing, it may become more difficult to examine LCD products with down-sized features by human eye inspection.

Figure 1:
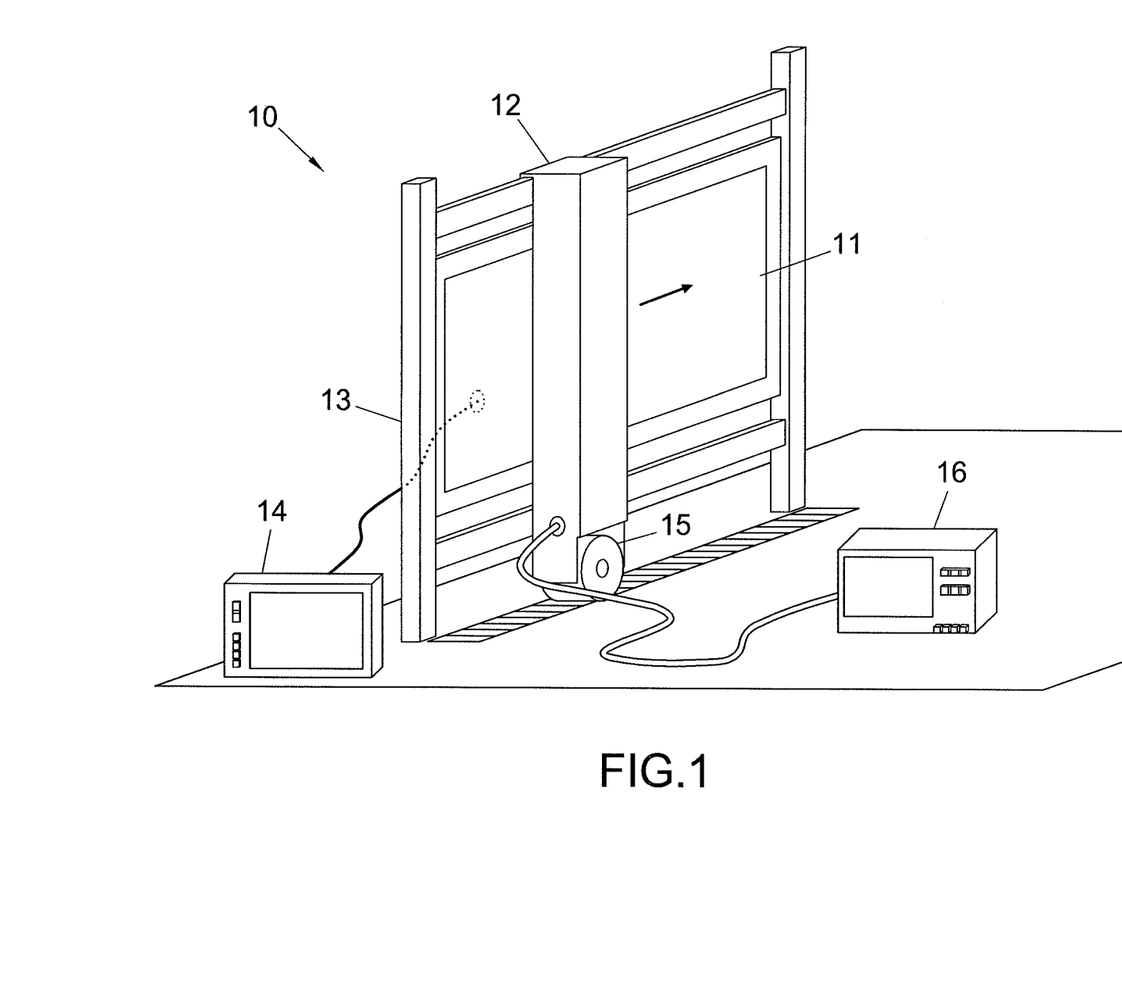
FIG. 1 is a reproduction of FIG. 1A of U.S. patent application Ser. No. 12/345,678.

An inspection system using a scanner for inspecting defects or features of an object has been disclosed in U.S. patent application Ser. No. 12/345,678 (hereinafter referred to as "the 678 application") entitled "Inspection System", filed Mar. 30, 2010 by the same inventors of the subject application. FIG. 1 is a reproduction of FIG. 1A of the 678 application, which illustrates a system 10 for optical inspection. Referring to FIG. 1, the system 10 may include a product under inspection such as a panel 11, a scanner 12, a signal generator 14, an analyzing device 16 and a support frame 13. The panel 11 to be inspected may be placed in the support frame 13 by, for example, an operator. However, prior to inspection, a warm-up process for the panel 11 may generally be conducted to ensure the quality of inspection. Depending on panel size, the warm-up may take, for example, 20 seconds and may thus slow down the inspection progress.

It may therefore be desirable to have a support mechanism that can facilitate a continuous inspection without compromise of inspection quality.

BRIEF SUMMARY OF THE INVENTION

Examples of the present invention may provide a support mechanism to support panels for an optical scan by a scanner in an inspection system. The support mechanism includes a first work frame to provide a first scanning area for a first scanner, a first frame to support a first panel, the first frame pivotably coupled to a first end of the first work frame so that the first frame is rotatable about the first end of the first work frame between a folded position that the first frame is folded toward the first scanning area and an unfolded position that the first frame is away from the first scanning area, and a second frame to support a second panel, the second frame pivotably coupled to a second end of the first work frame so that the second frame is rotatable about the second end of the first work frame between a folded position that the second frame is folded toward the first scanning area and an unfolded position that the second frame is away from the first scanning area, wherein the first scanning area allows the first scanner to scan across one of the first and second frames when the one of the first and second frames is at the folded position while the other one of the first and second frames is at the unfolded position.

Some examples of the present invention may also provide a support mechanism to support panels for an optical scan by a scanner in an inspection system. The support mechanism includes a first work frame to provide a first scanning area for a first scanner, a second work frame to provide a second scanning area for the first scanner, a first frame to support a first panel, the first frame pivotably coupled to a first end of the first work frame so that the first frame is rotatable about the first end of the first work frame between a folded position that the first frame is folded toward the first scanning area and an unfolded position that the first frame is away from the first scanning area, a second frame to support a second panel, the second frame pivotably coupled to a first end of the second work frame so that the second frame is rotatable about the first end of the second work frame between a folded position that the second frame is folded toward the second scanning area and an unfolded position that the second frame is away from the second scanning area, and a rotator to rotate the first scanner so that the first scanner is adapted to scan across the first frame in one direction and scan across the second frame in the reverse direction.

Examples of the present invention may still provide a support mechanism to support panels for an optical scan by a scanner in an inspection system. The support mechanism includes a first work frame to provide a first scanning area for a first scanner, a second work frame, extending in parallel with the first work frame, to provide a second scanning are for a second scanner, a first frame to support a first panel, the first frame pivotably coupled to a first end of the first work frame so that the first frame is rotatable about the first end of the first work frame between a folded position that the first frame is folded toward the first scanning area and an unfolded position that the first frame is away from the first scanning area, a second frame to support a second panel, the second frame pivotably coupled to a second end of the first work frame so that the second frame is rotatable about the second end of the first work frame between a folded position that the second frame is folded toward the first scanning area and an unfolded position that the second frame is away from the first scanning area, a third frame to support a third panel, the third frame pivotably coupled to a first end of the second work frame so that the third frame is rotatable about the first end of the second work frame between a folded position that the third frame is folded toward the second scanning area and an unfolded position that the third frame is away from the second scanning area, and a fourth frame to support a fourth panel, the fourth frame pivotably coupled to a second end of the second work frame so that the fourth frame is rotatable about the second end of the second work frame between a folded position that the fourth frame is folded toward the second scanning area and an unfolded position that the fourth frame is away from the second scanning area.

Additional features and advantages of the present invention will be set forth in portion in the description which follows, and in portion will be obvious from the description, or may be learned by practice of the invention. The features and advantages of the invention will be realized and attained by means of the elements and combinations particularly pointed out in the appended claims.

It is to be understood that both the foregoing general description and the following detailed description are exemplary and explanatory only and are not restrictive of the invention as claimed.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, examples are shown in the drawings. It should be understood, however, that the invention is not limited to the precise arrangements and instrumentalities shown in the examples.

In the drawings.

DETAILED DESCRIPTION OF THE INVENTION

Reference will now be made in detail to the present examples of the invention, examples of which are illustrated in the accompanying drawings. Wherever possible, the same reference numbers will be used throughout the drawings to refer to the same or like parts.

Figure 2A:
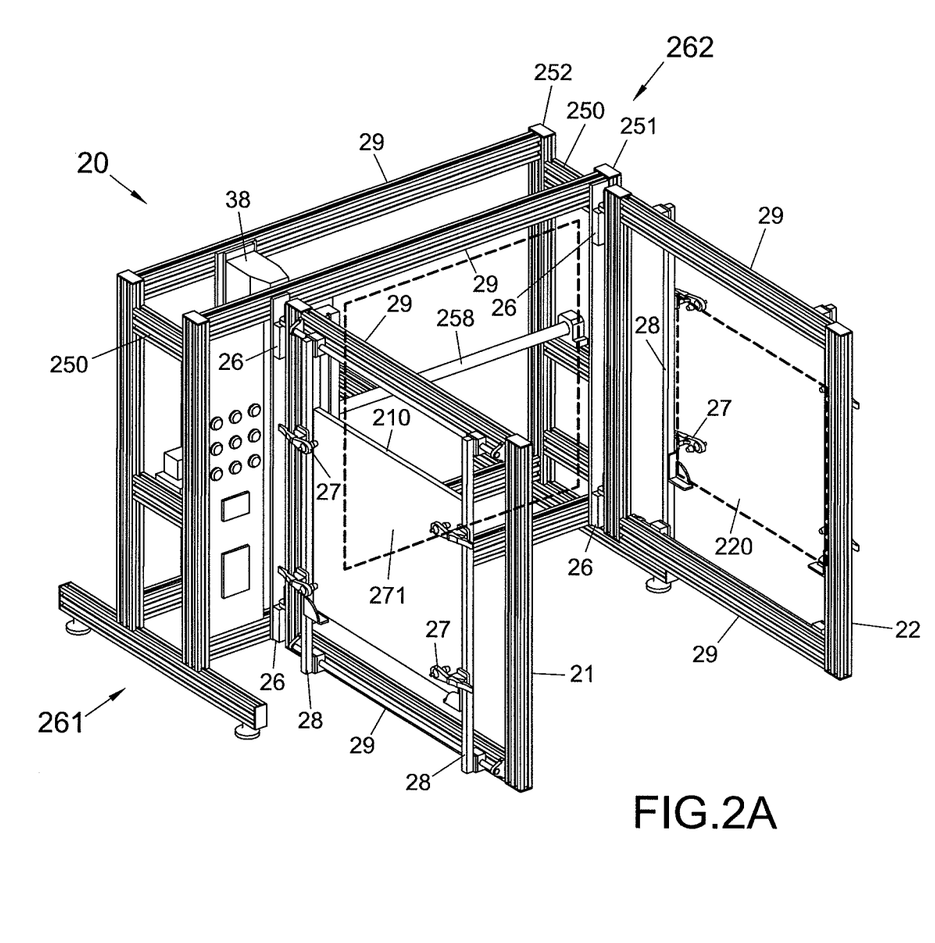
FIG. 2A is a perspective view of a support mechanism in accordance with an example of the present invention.

FIG. 2A is a perspective view of a support mechanism 20 in accordance with an example of the present invention. Referring to FIG. 2A, the support mechanism 20 may include a first frame 21, a second frame 22 and a first work frame 251. Each of the first frame 21, second frame 22 and first work frame 251 may take the form of a substantially rectangular shape. The first work frame 251 may provide a first scanning area 271 for a first scanner 38 to scan across a panel. The first and second frames 21 and 22 may be adapted to support a first panel 210 and a second panel 220, respectively. Specifically, taking the first frame 21 as an example, the first panel 210 may be secured by fixtures 27 to a pair of poles 28, which in turn may be secured to a pair of brackets 29 of the first frame 21. The poles 28 may extend in parallel in a first direction and may be separated from each other by a desired distance to fit the size of the first panel 210. The brackets 29 of the first frame 21 may extend in parallel in a second direction substantially orthogonal to the first direction and may be adapted to hold the poles 28 in place. The structure of the brackets 29 will be described in detail in later paragraphs with reference to FIGS. 5A and 5B.

The first frame 21 may be pivotably coupled to a first end 261 of the first work frame 251 by hinges 26. Accordingly, the first frame 21 may be rotatable about the first end 261 of the first work frame 251 between a folded position that the first frame 21 is folded toward the first scanning area 271 and an unfolded position that the first frame 21 is away from the first scanning area 271. Likewise, the second frame 22 may be pivotably coupled to a second end 262 of the first work frame 251 by hinges 26 and thus may be rotatable about the second end 262 of the first work frame 251 between a folded position that the second frame 22 is folded toward the first scanning area 271 and an unfolded position that the second frame 22 is away from the first scanning area 271.

The scanner 38, which may include but is not limited to the exemplary scanner 12 described and illustrated in the 678 application, may move along a rail 258 extending in a direction from the first end 261 to the second end 262 of the first work frame 251. Accordingly, when one of the first frame 21 and the second frame 22 is folded toward the first work frame 251, the scanner 38 may scan across the first panel 210 or the second panel 220 in a direction from the first end 261 to the second end 262 or vice versa.

The support mechanism 20 may also include a second work frame 252, which may be similar in structure to the first work frame 251. The second work frame 252 may extend in parallel with the first work frame 251 and may provide a second scanning area 272 for the scanner 38 or another scanner. The first and second work frames 251 and 252 may be separated from each other by a number of ribs 250 and may thus define a space where the scanner 38 may move along the rail 258.

Figure 2B:
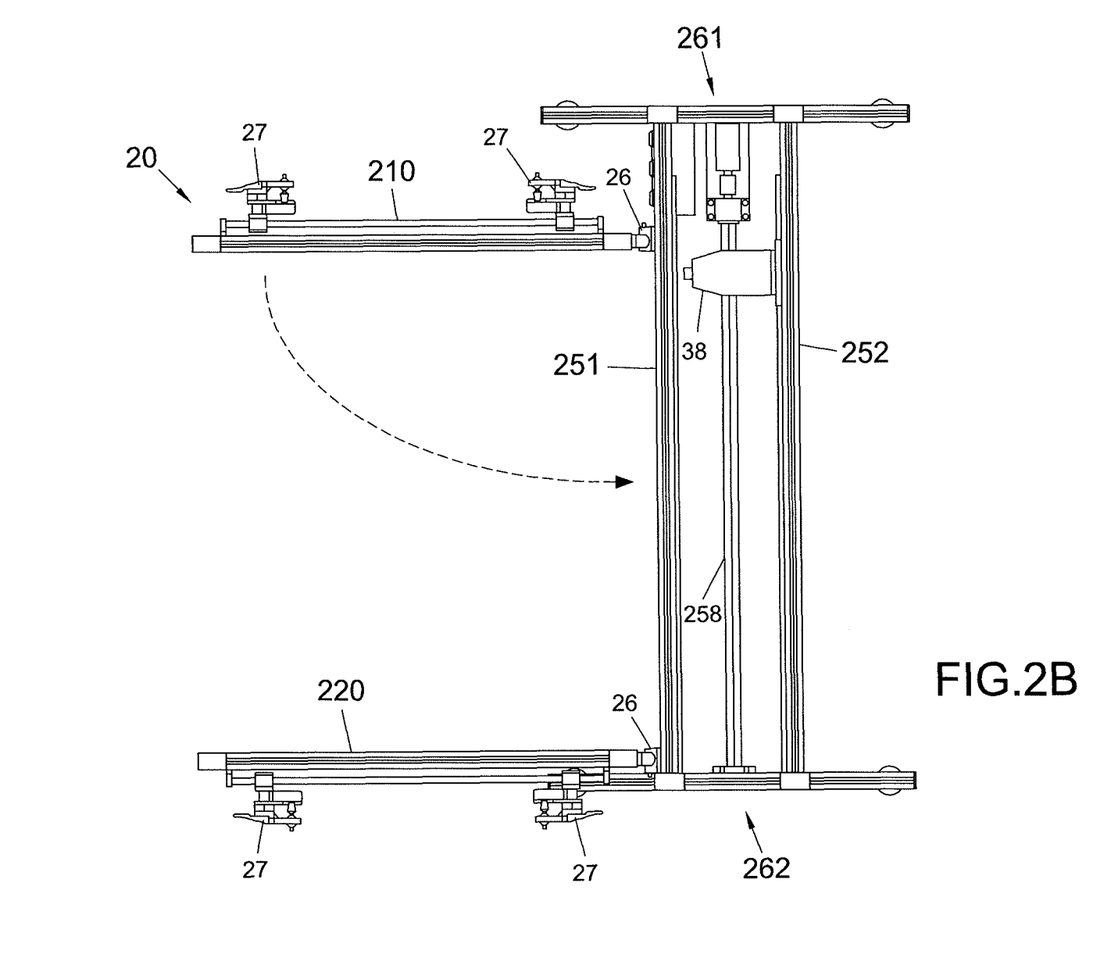
FIG. 2B is a top view of the support mechanism illustrated in FIG. 2A.

FIG. 2B is a top view of the support mechanism 20 illustrated in FIG. 2A. It may be assumed that the first panel 210 has been placed on the first frame 21 and conducted a warm-up in a setting process and is ready for inspection, and the second panel 220 is ready to take a setting process. Referring to FIG. 2B, in operation, the first frame 21 and hence the first panel 210 may be folded toward the first work frame 251, as indicated in a dash-line arrow. The scanner 38 may then move along the rail 258 and scan across the first panel 210. At the same time the first frame 21 is folded, the second panel 220 may be placed on the second frame 22 and then subjected to a warm-up.

After scanning, the first panel 210 may be removed from the first frame 21, which in turn may be unfolded from the first work frame 251 to a setting position. When the setting process is done, the second frame 22 together with the second panel 220 may be folded toward the first work frame 251. Next, after the second frame 22 is folded, another panel may be placed on the first frame 21 and then subjected to a warm-up. As a result, while one panel 21 is under inspection, another panel 22 is under setting, which may facilitate a continuous inspection for a series of panels.

Figure 3:
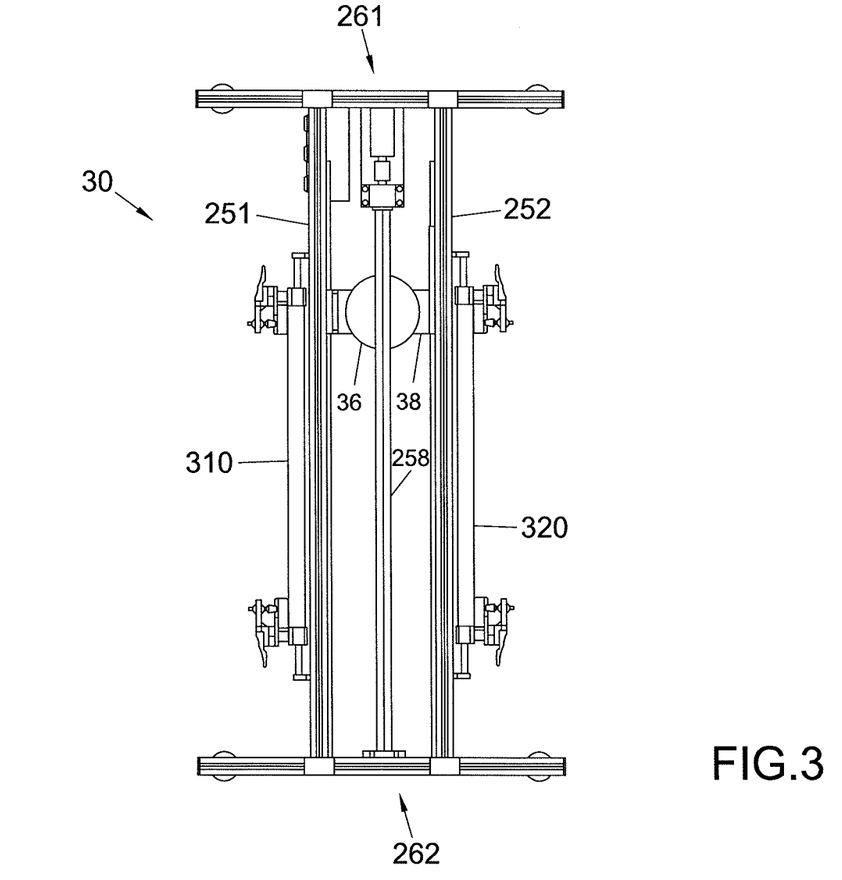
FIG. 3 is a top view of a support mechanism in accordance with another example of present application.

FIG. 3 is a top view of a support mechanism 30 in accordance with another example of present application. Referring to FIG. 3, the support mechanism 30 may, similar to the support mechanism 20 illustrated in FIG. 2A, include the first work frame 251, second work frame 252 and scanner 38. However, while the first frame 21 is pivotably coupled to the first work frame 251, the second frame 22 is pivotably coupled to the second work frame 252. In operation, the first frame 21 and the second frame 22 may be folded toward the first work frame 251 and the second work frame 252, respectively. The scanner 38 may then move along the rail 258 from a start point and scan, for example, a first panel 310 on the first frame 21 at one side of the rail 258. After the first panel 310 is scanned, the scanner 38 may turn about with the help of a rotator 36 to scan a second panel 320 on the second frame 22 at the other side of the rail 258 on its way back to the start point.

In the present example, one first panel 310 and one second panel 320 are scanned. In other examples, however, a number of first panels at one side of the rail 258 and a number of second panels at the other side of the rail 258 may be scanned as the scanner 38 moves along the rail 258 in a round trip.

Figure 4A:
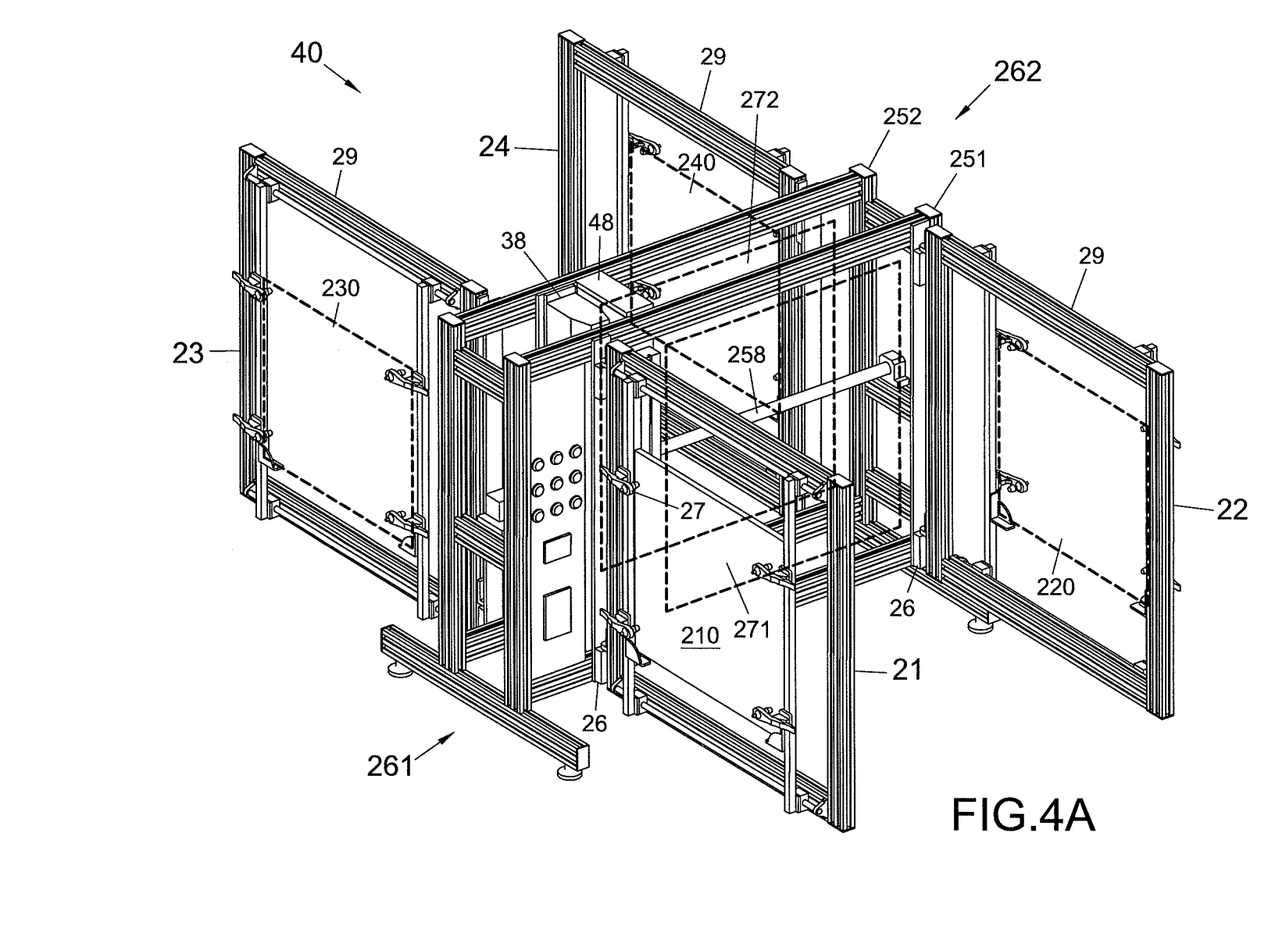
FIG. 4A is a perspective view of a support mechanism in accordance with yet another example of the present invention.

FIG. 4A is a perspective view of a support mechanism 400 in accordance with yet another example of the present invention. Referring to FIG. 4A, the support mechanism 400 may be similar to the support mechanism 20 described and illustrated with reference to FIG. 2A except that, for example, a third frame 23 and a fourth frame 24 may be added. Specifically, the third and fourth frames 23 and 24 may be pivotably coupled to a first end 261 and a second end 262 of the second work frame 252, respectively, by hinges. Accordingly, the third frame 23 may be rotatable about the first end 261 of the second work frame 252 between a folded position that the third frame 23 is folded toward the second scanning area 272 and an unfolded position that the third frame 23 is away from the second scanning area 272. Likewise, the fourth frame 24 may be rotatable about the second end 262 of the second work frame 252 between a folded position that the fourth frame 24 is folded toward the second scanning area 272 and an unfolded position that the fourth frame 24 is away from the second scanning area 272.

Furthermore, in the present example, in addition to the first scanner 38, a second scanner 48 may be provided, which may also move alone the rail 258 to scan a third panel 230 on the third frame 23 or a fourth panel 240 on the fourth frame 24. In other examples, however, a single scanner 38 may be used to scan the panels 2210 to 240 respectively on the frames 21 to 24 with the help of a rotator such as the rotator 36 illustrated in FIG. 3.

Figure 4B:
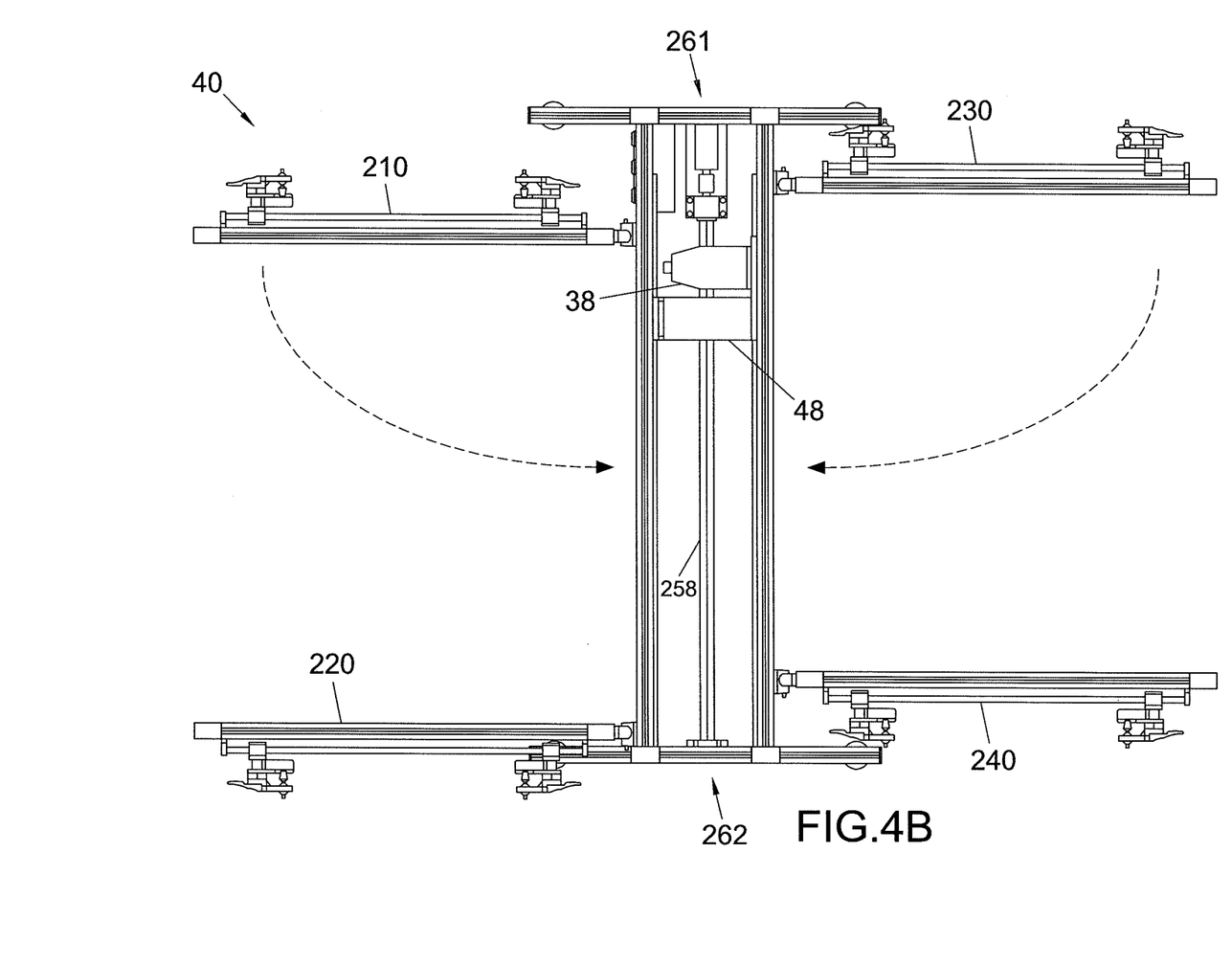
FIG. 4B is a top view of the support mechanism illustrated in FIG. 4A.

FIG. 4B is a top view of the support mechanism 40 illustrated in FIG. 4A. It may be assumed that the first and third panels 210 and 230 have been placed on the first and third frames 21 and 23 respectively and conducted a warm-up in a setting process and thus is ready for inspection, and the second and fourth panels 220 and 240 are ready to take a setting process. Referring to FIG. 4B, in operation, the first frame 21 and hence the first panel 210 may be folded toward the first work frame 251, as indicated in a dash-line arrow. Furthermore, the third frame 23 and hence the third panel 230 may be folded toward the second work frame 252, as indicated in another dash-line arrow. The first scanner 38 and the second scanner 48 may then move along the rail 258 and scan across the first panel 210 and the third panel 230, respectively.

At the same time the first frame 21 is folded, the second panel 220 may be placed on the second frame 22 and then subjected to a warm-up. Similarly, at the same time the third frame 23 is folded, the fourth panel 240 may be placed on the fourth frame 24 and then subjected to a warm-up.

After scanning, the first panel 210 may be removed from the first frame 21, which in turn may be unfolded from the first work frame 251 to a setting position. Moreover, the third panel 230 may be removed from the third frame 23, which in turn may be unfolded from the second work frame 252 to a setting position.

Subsequently, when the setting process is done, the second frame 22 together with the second panel 220 may be folded toward the first work frame 251. Next, after the second frame 22 is folded, another panel may be placed on the first frame 21 and then subjected to a warm-up. Similarly, when the setting process is done, the fourth frame 24 together with the fourth panel 240 may be folded toward the second work frame 252. Next, after the fourth frame 24 is folded, another panel may be placed on the third frame 23 and then subjected to a warm-up.

As a result, while a first pair of panels 21 and 23 is under inspection, a second pair of panels 22 and 24 is under setting, which may facilitate a continuous inspection for a series of panels.

Figures 5A, 5B:
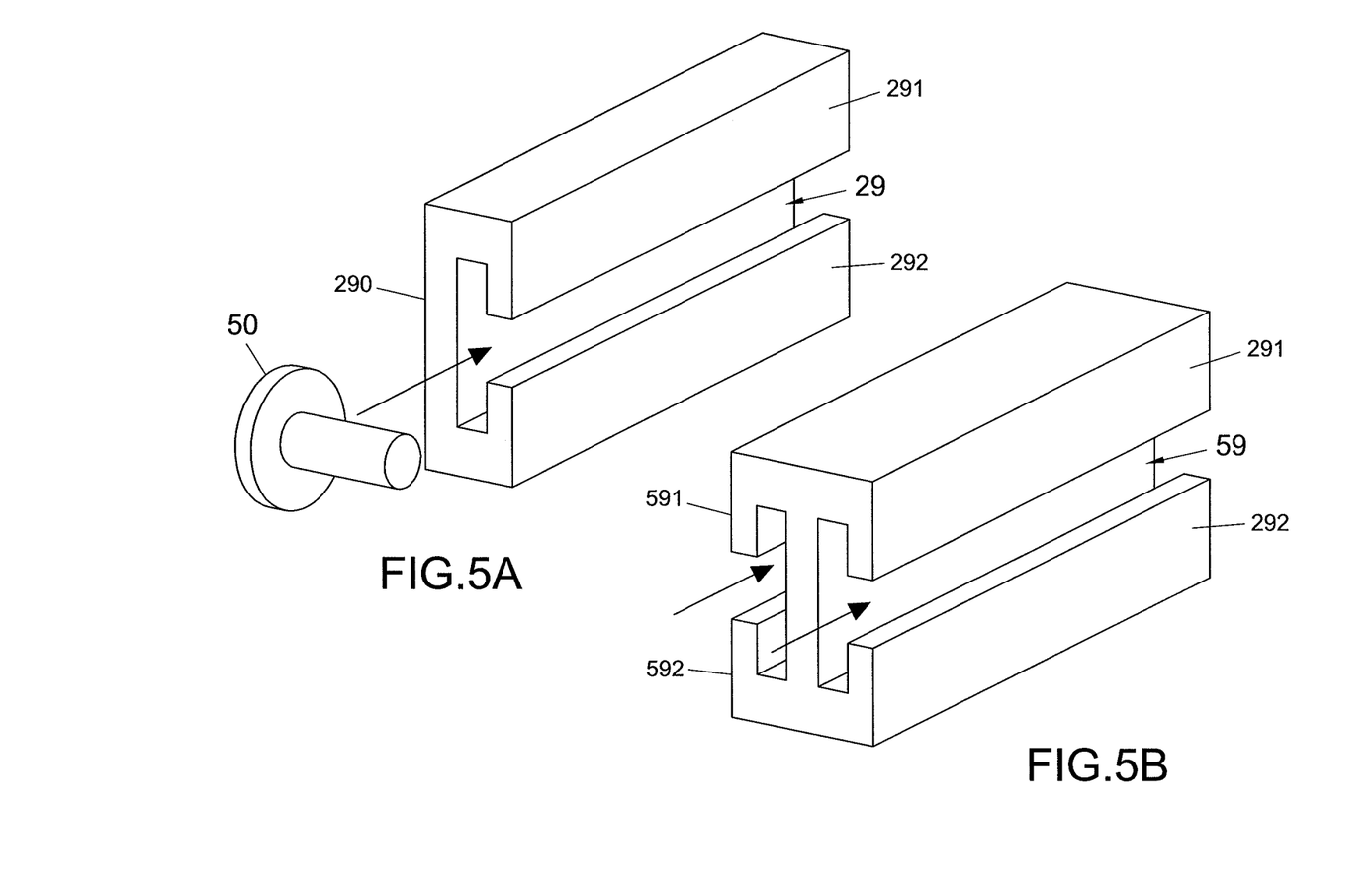
FIG. 5A is a perspective view of a bracket in a support mechanism in accordance with an example of the present invention.
FIG. 5B is a perspective view of a bracket in a support mechanism in accordance with another example of the present invention.

FIG. 5A is a perspective view of the bracket 29 in the support mechanism 20 illustrated in FIG. 2A in accordance with an example of the present invention. Referring to FIG. 5A, the bracket 29 may include a base 290 and a pair of flanges 291 and 292 opposed to each other, thus defining a chamber (not numbered) associated with the base 290 and a slot (not numbered) between the flanges 291 and 292. The bracket 29 may hold the pole 28 in place with the help of fastening elements such as bolts and nuts. Specifically, the head of a bolt 50 may be held in the chamber while the shaft of the bolt 50 may protrude from the slot to engage with a nut so that one end of the pole 28 may be secured.

FIG. 5B is a perspective view of a bracket 59 in a support mechanism in accordance with another example of the present invention. Referring to FIG. 5B, the bracket 59, in addition to a first chamber and slot defined by the first pair of flanges 291 and 292, has a second chamber and slot defined by a second pair of flanges 591 and 592.

It will be appreciated by those skilled in the art that changes could be made to the examples described above without departing from the broad inventive concept thereof. It is understood, therefore, that this invention is not limited to the particular examples disclosed, but it is intended to cover modifications within the spirit and scope of the present invention as defined by the appended claims.

Further, in describing representative examples of the present invention, the specification may have presented the method and/or process of the present invention as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process of the present invention should not be limited to the performance of their steps in the order written, and one skilled in the art can readily appreciate that the sequences may be varied and still remain within the spirit and scope of the present invention.

We claim:

1. A support mechanism to support panels for an optical scan by a scanner in an inspection system, the support mechanism comprising:

a first work frame to provide a first scanning area for a first scanner;

a second work frame, extending in parallel with the first work frame, to provide a second scanning area for the first scanner;

a first frame to support a first panel, the first frame pivotably coupled to the first work frame near a first end of the first work frame so that the first frame is rotatable about the first work frame between a folded position that the first frame is folded parallel to the first scanning area and an unfolded position that the first frame is away from the first scanning area;

a second frame to support a second panel, the second frame pivotably coupled to the second work frame near a first end of the second work frame, so that the second frame is rotatable about the second work frame between a folded position that the second frame is folded parallel to the second scanning area and an unfolded position that the second frame is away from the second scanning area, or pivotably coupled to the first work frame near a second end of the first work frame, so that the second frame is rotatable about the first work frame between a folded position that the second frame is folded parallel to the first scanning area and an unfolded position that the second frame is away from the first scanning area, and given that the second frame is pivotably coupled to the first work frame, the first scanner is adapted to scan across the first frame in one direction and scan across the second frame in the reverse direction, or given that the second frame is pivotably coupled to the second work frame, the support mechanism further comprising a rotator to rotate the first scanner so that the first scanner is adapted to scan across the first frame in one direction when the first frame is at the folded position, and scan across the second frame in the reverse direction when the second frame is at the folded position;

a rail extending in a direction from the first end to the second end, wherein the rail allows the first scanner to move between the first and second ends of the first work frame; and a third frame to support a third panel, the third frame pivotably coupled to the second work frame near the first end of the second work frame so that the third frame is rotatable about the second work frame between a folded position that the third frame is folded toward the second scanning area and an unfolded position that the third frame is away from the second scanning area, wherein the rotator rotates the first scanner so that the first scanner is adapted to scan across one of the first and second frames when moves in one direction and scan across the third frame when moves in the reverse direction.

2. The support mechanism of claim 1 further comprising a fourth frame to support a fourth panel, the fourth frame pivotably coupled to the second work frame near a second end of the second work frame so that the fourth frame is rotatable about the second work frame between a folded position that the fourth frame is folded toward the second scanning area and an unfolded position that the fourth frame is away from the second scanning area.

3. The support mechanism of claim 2, wherein the second scanning area allows the first scanner to scan across one of the third and fourth frames when the one of the third and fourth frames is at the folded position while the other one of the third and fourth frames is at the unfolded position.

4. The support mechanism of claim 3, wherein the rail extends in a space between the first work frame and the second work frame, wherein the rail allows the first scanner to move between the first and second ends of the first work frame in the one direction and move between the first and second ends of the second work frame in the reverse direction.

5. A support mechanism to support panels for an optical scan by a scanner in an inspection system, the support mechanism comprising:

a first work frame to provide a first scanning area for a first scanner;

a second work frame, extending in parallel with the first work frame, to provide a second scanning area for the first scanner;

a first frame to support a first panel, the first frame pivotably coupled to the first work frame near a first end of the first work frame so that the first frame is rotatable about the first work frame between a folded position that the first frame is folded toward the first scanning area and an unfolded position that the first frame is away from the first scanning area;

a second frame to support a second panel, the second frame pivotably coupled to the second work frame near a first end of the second work frame so that the second frame is rotatable about the second work frame between a folded position that the second frame is folded toward the second scanning area and an unfolded position that the second frame is away from the second scanning area; and a third frame to support a third panel, the third frame pivotably coupled to the first work frame near a second end of the first work frame so that the third frame is rotatable about the first work frame between a folded position that the third frame is folded toward the first scanning area and an unfolded position that the third frame is away from the first scanning area, a rotator to rotate the first scanner so that the first scanning area allows the first scanner to scan across one of the first and third frames when the rotator moves in one direction and when the one of the first and third frames is at the folded position while the other one of the first and third frames is at the unfolded position, and so that the second scanning area allows the first scanner to scan across the second frame when the rotator moves in the reverse direction and when the second frame is at the folded position.

6. A support mechanism to support panels for an optical scan by a scanner in an inspection system, the support mechanism comprising:

a first work frame to provide a first scanning area for a first scanner;

a second work frame, extending in parallel with the first work frame, to provide a second scanning area for the first scanner;

a first frame to support a first panel, the first frame pivotably coupled to the first work frame near a first end of the first work frame so that the first frame is rotatable about the first work frame between a folded position that the first frame is folded toward the first scanning area and an unfolded position that the first frame is away from the first scanning area;

a second frame to support a second panel, the second frame pivotably coupled to the first work frame near a second end of the first work frame so that the second frame is rotatable about the first work frame between a folded position that the second frame is folded toward the first scanning area and an unfolded position that the second frame is away from the first scanning area;

a third frame to support a third panel, the third frame pivotably coupled to the second work frame near a first end of the second work frame so that the third frame is rotatable about the second work frame between a folded position that the third frame is folded toward the second scanning area and an unfolded position that the third frame is away from the second scanning area;

a rail extending in a direction from the first side to the second side, wherein the rail allows the first scanner to move between the first and second sides of the first work frame; and a rotator to rotate the first scanner so that the first scanner is adapted to scan across one of the first and second frames when moves in one direction and scan across the third frame when moves in the reverse direction.

7. A support mechanism to support panels for an optical scan by a scanner in an inspection system, the support mechanism comprising:

(i) a first work frame to provide a first scanning area for a first scanner;

(ii) a second work frame, extending in parallel with the first work frame, to provide a second scanning area for the first scanner;

(iii) a first frame to support a first panel, the first frame pivotably coupled to the first work frame near a first end of the first work frame so that the first frame is rotatable about the first work frame between a folded position that the first frame is folded parallel to the first scanning area and an unfolded position that the first frame is away from the first scanning area;

(iv) a second frame to support a second panel, the second frame pivotably coupled to the second work frame near a first end of the second work frame, so that the second frame is rotatable about the second work frame between a folded position that the second frame is folded parallel to the second scanning area and an unfolded position that the second frame is away from the second scanning area, or pivotably coupled to the first work frame near a second end of the first work frame, so that the second frame is rotatable about the first work frame between a folded position that the second frame is folded parallel to the first scanning area and an unfolded position that the second frame is away from the first scanning area, and given that the second frame is pivotably coupled to the first work frame, the first scanner is adapted to scan across the first frame in one direction and scan across the second frame in the reverse direction, or given that the second frame is pivotably coupled to the second work frame, the support mechanism further comprising a rotator to rotate the first scanner so that the first scanner is adapted to scan across the first frame in one direction when the first frame is at the folded position, and scan across the second frame in the reverse direction when the second frame is at the folded position, (v) a third frame to support a third panel, given that the second frame is pivotably coupled to the second work frame, the third frame is configured to pivotably couple to the first work frame near a second end of the first work frame, so that the third frame is rotatable about the first work frame between a folded position that the third frame is folded toward the first scanning area and an unfolded position that the third frame is away from the first scanning area, or given that the second frame is pivotably coupled to the first work frame, the third frame is configured to pivotably couple to the second work frame near a first end of the second work frame, so that the third frame is rotatable about the second work frame between a folded position that the third frame is folded toward the second scanning area and an unfolded position that the third frame is away from the second scanning area; wherein given that the second frame is pivotably coupled to the second work frame, the first scanning area allows the first scanner to scan across one of the first and third frames when the one of the first and third frames is at the folded position while the other one of the first and third frames is at the unfolded position, or given that the second frame is pivotably coupled to the first work frame, the first scanning area allows the first scanner to scan across one of the first and second frames when the one of the first and second frames is at the folded position while the other one of the first and second frames is at the unfolded position; and (vi) a fourth frame to support a fourth panel, the fourth frame pivotably coupled to the second work frame near a second end of the second work frame so that the fourth frame is rotatable about the second work frame between a folded position that the fourth frame is folded toward the second scanning area and an unfolded position that the fourth frame is away from the second scanning area, wherein given that the second frame is pivotably coupled to the second work frame, the second scanning area allows a second scanner to scan across one of the second and fourth frames when the one of the second and fourth frames is at the folded position while the other one of the second and fourth frames is at the unfolded position, or given that the second frame is pivotably coupled to the first work frame, the second scanning area allows the second scanner to scan across one of the third and fourth frames when the one of the third and fourth frames is at the folded position while the other one of the third and fourth frames is at the unfolded position.

* * * * *